United States Patent [19]

Ishikawa et al.

[11] 4,293,694
[45] Oct. 6, 1981

[54] PYRIDO[3,2,1-JK]CARBAZOLS

[75] Inventors: Hiroshi Ishikawa; Kazuyuki Nakagawa, both of Tokushima, Japan

[73] Assignee: Otsuka Pharmaceutical Co., Ltd., Tokyo, Japan

[21] Appl. No.: 28,771

[22] Filed: Apr. 10, 1979

[51] Int. Cl.³ .......................................... C07D 221/04
[52] U.S. Cl. ..................................... 546/72; 424/258
[58] Field of Search ........................................ 546/72

[56] References Cited
U.S. PATENT DOCUMENTS
3,985,882 10/1976 Gerster ................................ 424/258

Primary Examiner—Donald G. Daus
Assistant Examiner—D. B. Springer
Attorney, Agent, or Firm—Sughrue, Mion, Zinn, Macpeak & Seas

[57] ABSTRACT

A pyrido[3,2,1-jk]carbazol derivative represented by the formula (I)

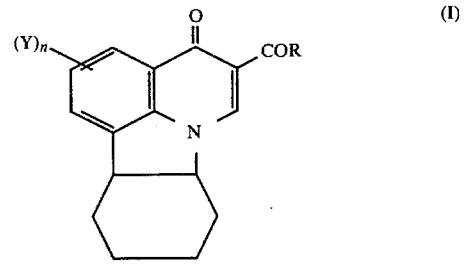

wherein R represents a hydroxy group, an alkoxy group which may be substituted with a halogen atom or with a 4-methyl-1-piperidinyl group, a hydrazino group or a

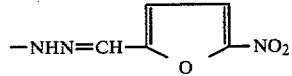

group, Y represents an alkoxy group, a halogen atom, a nitro group, an amino group, an alkanoylamino group or alkyl group, and n is 0, 1 or 2; and the pharmaceutically acceptable salts thereof having antimicrobial, anticancer and antiviral activities, and a process for preparing the same.

14 Claims, No Drawings

PYRIDO[3,2,1-JK]CARBAZOLS

BACKGROUND OF THE INVENTION

1. Field of the Invention

This invention relates to pyrido[3,2,1-jk]carbazol derivatives represented by the formula (I) hereinafter defined and the pharmaceutically acceptable salts thereof which are useful as antimicrobial, anti-cancer and antiviral agents, a process for preparing the same and a pharmaceutical composition containing pyrido[3,2,1-jk]carbazol derivative.

2. Description of the Prior Art

It is known that certain types of polyheterocyclic compounds exhibit antimicrobial activities. For example, Gerster et al U.S. Pat. No. 3,917,609 discloses substituted derivatives of 1,2-dihydro-6-oxo-6H-pyrrolo[3,2,1-ij]quinoline which are useful as antimicrobial agents or as intermediates for the preparation of antimicrobial agents.

Also, Gerster et al U.S. Pat. Nos. 3,896,131; 3,985,882; 3,969,463; 4,001,243 and 4,014,877 disclose 6,7-dihydro-1-oxo-1H, 5H-benzo[ij]quinolizine derivatives having antimicrobial activities.

However, the pyrido[3,2,1-jk]carbazol derivatives of the present invention are structurally different from these quinoline and quinolizine compounds.

SUMMARY OF THE INVENTION

Accordingly, it is one object of the present invention to provide a pyrido[3,2,1-jk]carbazol derivative having high antimicrobial effects and low toxicity.

It is another object of the present invention to provide a pharmaceutical composition comprising these pyrido[3,2,1-jk]-carbazol derivatives or pharmaceutically acceptable salts thereof in therapeautically effective amounts.

Still another object of the present invention is to provide a process for preparing the aforesaid derivatives.

Accordingly, the present invention provides a pyrido[3,2,1-jk]carbazol derivative represented by the formula [I]

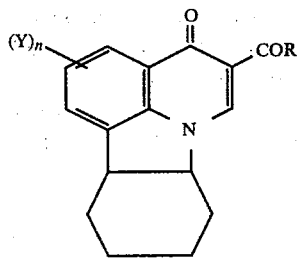

wherein R represents a hydroxy group, an alkoxy group which may be substituted with a halogen atom or with a 4-methyl-1-piperidinyl group, a hydrazino group or a

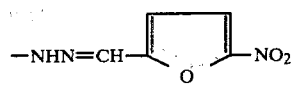

group, Y represents an alkoxy group, a halogen atom, a nitro group, an amino group, an alkanoylamino group or alkyl group, and n is 0, 1 or 2; and the pharmaceutically acceptable salts thereof having antimicrobial, anti-cancer and antiviral activity.

DETAILED DESCRIPTION OF THE INVENTION

The term "alkyl" as used herein refers to a straight or branched chain alkyl group having 1 to 4 carbon atoms such as methyl, ethyl, propyl, isopropyl, butyl, tert-butyl groups.

The term "alkoxy" as used herein refers to a straight or branched alkoxy group having 1 to 4 carbon atoms such as methoxy, ethoxy, propoxy, isopropoxy, butoxy, tert-butoxy groups.

The term "halogen" as used herein includes a chlorine atom, a bromine atom, an iodine atom and a fluorine atom.

The term "alkanoylamino" as used herein refers to a straight or branched alkanoylamine group having 1 to 4 carbon atoms such as an acetylamino group, a propanoylamino group, a butanoylamino group, an isobutanoylamino group and the like.

The term "an alkoxy group which may be substituted with a halogen atom or with a 4-methyl-1-piperazinyl group" as used herein for R means the alkoxy group as defined above which may be substituted with a halogen atom or a 4-methyl-1-piperazinyl group and includes methoxy, ethoxy, propoxy, isopropoxy, butoxy, tert-butoxy, monochloromethoxy, 2-bromoethoxy, 3-bromopropoxy, 4-fluorobutoxy, 3-chloro-2-methylpropoxy, 2-fluoroethoxy, 2-(4-methyl-1-piperidinyl)ethoxy, 3-(4-methyl-1-piperidinyl)propoxy, 4-(4-methyl-1-piperidinyl)butoxy, 3-(4-methyl-1-piperidinyl)-2-methylpropoxy and the like groups.

The pyrido[3,2,1-jk]carbazol derivatives represented by the formula (I) above are novel compounds and these compounds as well as the pharmaceutically acceptable salts thereof are useful as antimicrobial, anti-cancer and anti-viral agents.

Representative compounds of the present invention included in the formula (I) are as follows:

Ethyl 7a,8,9,10,11,11a-hexahydro-4-oxo-4H-pyrido[3,2,1-jk]carbazol-5-carboxylate,
7a,8,9,10,11,11a-Hexahydro-4-oxo-4H-pyrido[3,2,1-jk]carbazol-5-carboxylic acid,
Propyl 7a,8,9,10,11,11a-hexahydro-4-oxo-4H-pyrido[3,2,1-jk]carbazol-5-carboxylate,
Isopropyl 7a,8,9,10,11,11a-hexahydro-4-oxo-4H-pyrido[3,2,1-jk]carbazol-5-carboxylate,
2-Methyl-7a,8,9,10,11,11a-hexahydro-4-oxo-4H-pyrido[3,2,1-jk]carbazol-5-carboxylic acid,
2-Propyl-7a,8,9,10,11,11a-hexahydro-4-oxo-4H-pyrido[3,2,1-jk]carbazol-5-carboxylic acid,
2-Isopropyl-7a,8,9,10,11,11a-hexahydro-4-oxo-4H-pyrido[3,2,1-jk]carbazol-5-carboxylic acid,
Ethyl 2-methyl-7a,8,9,10,11,11a-hexahydro-4-oxo-4H-pyrido[3,2,1-jk]carbazol-5-carboxylate,
Propyl 2-nitro-7a,8,9,10,11,11a-hexahydro-4-oxo-4H-pyrido[3,2,1-jk]carbazol-5-carboxylate,
Methyl 2-amino-7a,8,9,10,11,11a-hexahydro-4-oxo-4H-pyrido[3,2,1-jk]carbazol-5-carboxylate,
Butyl 2-acetylamino-7a,8,9,10,11,11a-hexahydro-4-oxo-4H pyrido[3,2,1-jk]carbazol-5-carboxylate,
Ethyl 2-fluoro-7a,8,9,10,11,11a-hexahydro-4-oxo-4H-pyrido[3,2,1-jk]carbazol-5-carboxylate,
Ethyl 1,3-dichloro-7a,8,9,10,11,11a-hexahydro-4-oxo-4H-pyrido[3,2,1-jk]carbazol-5-carboxylate, 2-Nitro-7a,8,9,10,11,11a-hexahydro-4-oxo-4H-pyrido[3,2,1-jk]carbazol-5-carboxylic acid,
2-Amino-7a,8,9,10,11,11a-hexahydro-4-oxo-4H-pyrido[3,2,1-jk]carbazol-5-carboxylic acid,
2-Acetylamino-7a,8,9,10,11,11a-hexahydro-4-oxo-4H-pyrido[3,2,1-jk]carbazol-5-carboxylic acid,
2-Propanoylamino-7a,8,9,10,11,11a-hexahydro-4-oxo-4H-pyrido[3,2,1-jk]carbazol-5-carboxylic acid,
2-Isobutanoylamino-7a,8,9,10,11,11a-hexahydro-4-oxo-4H-pyrido[3,2,1-jk]carbazol-5-carboxylic acid,
2-Chloro-7a,8,9,10,11,11a-hexahydro-4-oxo-4H-pyrido[3,2,1-jk]carbazol-5-carboxylic acid,
2-Bromo-7a,8,9,10,11,11a-hexahydro-4-oxo-4H-pyrido[3,2,1-jk]carbazol-5-carboxylic acid,
2-Iodo-7a,8,9,10,11,11a-hexahydro-4-oxo-4H-pyrido[3,2,1-jk]carbazol-5-carboxylic acid,
2-Fluoro-7a,8,9,10,11,11a-hexahydro-4-oxo-4H-pyrido[3,2,1-jk]carbazol-5-carboxylic acid,
1-Fluoro-7a,8,9,10,11,11a-hexahydro-4-oxo-4H-pyrido[3,2,1-jk]carbazol-5-carboxylic acid,
1-chloro-7a,8,9,10,11,11a-hexahydro-4-oxo-4H-pyrido[3,2,1-jk]carbazol-5-carboxylic acid,
1,2-Dichloro-7a,8,9,10,11,11a-hexahydro-4-oxo-4H-pyrido[3,2,1-jk]carbazol-5-carboxylic acid,
1,3-Dichloro-7a,8,9,10,11,11a-hexahydro-4-oxo-4H-pyrido[3,2,1-jk]carbazol-5-carboxylic acid,
1,3-Dimethyl-7a,8,9,10,11,11a-hexahydro-4-oxo-4H-pyrido[3,2,1-jk]carbazol-5-carboxylic acid,
1,2-Dimethyl-7a,8,9,10,11,11a-hexahydro-4-oxo-4H-pyrido[3,2,1-jk]carbazol-5-carboxylic acid,
1,2-Diacetylamino-7a,8,9,10,11,11a-hexahydro-4-oxo-4H-pyrido[3,2,1-jk]carbazol-5-carboxylic acid,
Ethyl 2-methoxy-7a,8,9,10,11,11a-hexahydro-4-oxo-4H-pyrido[3,2,1-jk]carbazol-5-carboxylate,
2-Methoxy-7a,8,9,10,11,11a-hexahydro-4-oxo-4H-pyrido[3,2,1-jk]carbazol-5-carboxylic acid,
1,2-Diethoxy-7a,8,9,10,11,11a-hexahydro-4-oxo-4H-pyrido[3,2,1-jk]carbazol-5-carboxylic acid,
2-Butoxy-7a,8,9,10,11,11a-hexahydro-4-oxo-4H-pyrido[3,2,1-jk]carbazol-5-carboxylic acid,
β-Bromoethyl 2-fluoro-7a,8,9,10,11,11a-hexahydro-4-oxo-4H-pyrido[3,2,1-jk]carbazol-5-carboxylate,
β-Chloroethyl 2-fluoro-7a,8,9,10,11,11a-hexahydro-4-oxo-4H-pyrido[3,2,1-jk]carbazol-5-carboxylate,
β-Bromoethyl 2-chloro-7a,8,9,10,11,11a-hexahydro-4-oxo-4H-pyrido[3,2,1-jk]carbazol-5-carboxylate,
α-Chloroethyl 2-fluoro-7a,8,9,10,11,11a-hexahydro-4-oxo-4H-pyrido[3,2,1-jk]carbazol-5-carboxylate,
γ-Bromopropyl 2-fluoro-7a,8,9,10,11,11a-hexahydro-4-oxo-4H-pyrido[3,2,1-jk]carbazol-5-carboxylate,
β-Fluoroethyl 2-fluoro-7a,8,9,10,11,11a-hexahydro-4-oxo-4H-pyrido[3,2,1-jk]carbazol-5-carboxylate,
β-Methyl-α-chloropropyl 7a,8,9,10,11,11a-hexahydro-4-oxo-4H-pyrido[3,2,1-jk]carbazol-5-carboxylate,
β-Chloroethyl 2-methyl-7a,8,9,10,11,11a-hexahydro-4-oxo-4H-pyrido[3,2,1-jk]carbazol-5-carboxylate,
β-Bromoethyl 2-methoxy-7a,8,9,10,11,11a-hexahydro-4-oxo-4H-pyrido[3,2,1-jk]carbazol-5-carboxylate,
γ-Bromopropyl 3-acetylamino-7a,8,9,10,11,11a-hexahydro-4-oxo-4H-pyrido[3,2,1-jk]carbazol-5-carboxylate,
1,3-Dimethyl-7a,8,9,10,11,11a-hexahydro-4-oxo-4H-pyrido[3,2,1-jk]carbazol-5-carbohydrazide,
2-Methoxy-7a,8,9,10,11,11a-hexahydro-4-oxo-4H-pyrido[3,2,1-jk]carbazol-5-carboxylic acid 5-nitrofurfurylidenehydrazide,
7a,8,9,10,11,11a-Hexahydro-4-oxo-4H-pyrido[3,2,1-jk]carbazolcarboxylic acid 5-nitrofurfurylidenehydrazide,
β-(4-Methyl-1-piperidinyl)ethyl 2-methoxy-7a,8,9,10,11,11a-hexahydro-4-oxo-4H-pyrido[3,2,1-jk]carbazol-5-carboxylate,
β-(4-Methyl-1-piperidinyl)ethyl 7a,8,9,10,11,11a-hexahydro-4-oxo-4H-pyrido[3,2,1-jk]carbazol-5-carboxylate,
β-(4-Methyl-1-piperidinyl)ethyl 1,3-dimethyl-7a,8,9,10,11,11a-hexahydro-4-oxo-4H-pyrido[3,2,1-jk]carbazol-5-carboxylate,
β-Methyl-γ-chloropropyl 2-fluoro-7a,8,9,10,11,11a-hexahydro-4-oxo-4H-pyrido[3,2,1-jk]carbazol-5-carboxylate,
2-Fluoro-7a,8,9,10,11,11a-hexahydro-4-oxo-4H-pyrido[3,2,1-jk]carbazol-5-carbohydrazide,
2-Fluoro-7a,8,9,10,11,11a-hexahydro-4-oxo-4H-pyrido[3,2,1-jk]carbazol-5-carboxylic acid 5-nitrofurfurylidenehydrazide,
β-(4-Methyl-1-piperazinyl)ethyl 2-fluoro-7a,8,9,10,11,11a-hexahydro-4-oxo-4H-pyrido[3,2,1-jk]carbazol-5-carboxylate,
α-(4-Methyl-1-piperidyl)methyl 2-fluoro-7a,8,9,10,11,11a-hexahydro-4-oxo-4H-pyrido[3,2,1-jk]carbazol-5-carboxylate,
β-(4-Methyl-1-piperidyl)ethyl 2-chloro-7a,8,9,10,11,11a-hexahydro-4-oxo-4H-pyrido[3,2,1-jk]carbazol-5-carboxylate,
γ(4-Methyl-1-piperidyl)propyl 2-fluoro-7a,8,9,10,11,11a-hexahydro-4-oxo-4H-pyrido[3,2,1-jk]carbazol-5-carboxylate,
β-Methyl-γ-(4-methyl-1-piperidyl)propyl 2-fluoro-7a,8,9,10,11,11a-hexahydro-4-oxo-4H-pyrido[3,2,1-jk]carbazol-5-carboxylate,
and the like.

The pyrido[3,2,1-jk]carbazol compounds of the present invention represented by the formula (I) can be prepared by various alternative procedures. A typical process for the preparation of the compounds of the formula (I) can be illustrated by the following Reaction Scheme-I.

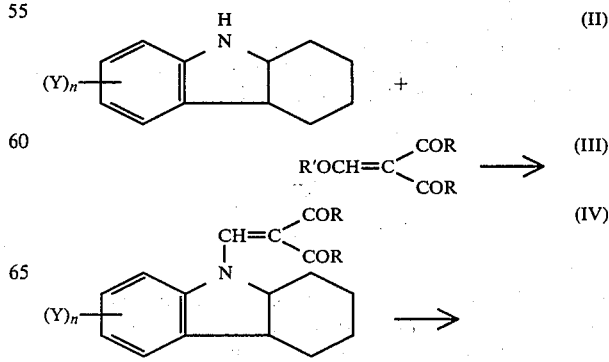

-continued

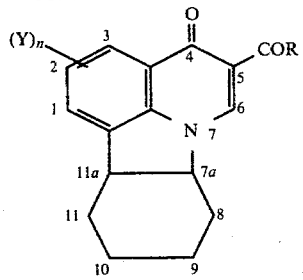

wherein Y, R and n are as defined above, R may be the same or different, and R' represents an alkyl group.

The above process can be illustrated hereinafter in greater detail.

The compounds of the formulae (II) and (III) used as starting materials in the above process are known compounds or can be easily prepared in accordance with the known procedures. The reaction between the compound of the formula (II) and the compound of the formula (III) can be effected in the absence of solvents or in the presence of solvents such as methanol, ethanol, isopropanol, acetonitrile, dimethylformamide, dimethyl sulfoxide, hexamethylphosphoric triamide and the like, preferably in the absence of solvents.

The compound of the formula (III) can be used in excess amounts over the equimolar amount relative to the compounds of the formula (II), preferably in an equimolar amount in the absence of solvents and in an amount of from 1.1 to 1.5 mol per mol of the compound of the formula (II) in the presence of solvents. The reaction can generally be carried out at a temperature of from room temperature (about 15° to 30° C.) to about 150° C., preferably 100° to 130° C., for a period of from about 0.5 to about 6 hours thereby easily yielding the compound represented by the formula (IV).

The subsequent cyclization reaction of the thus obtained compound of the formula (IV) can be effected in accordance with a conventional cyclization reaction, for example, a method comprising heating the compound of the formula (IV) or a cyclization method used an acidic substance such as phosphorus oxychloride, phosphorus pentachloride, phosphorus trichloride, thionyl chloride, concentrated sulfuric acid, polyphosphoric acid and the like. When the cyclization is effected by heating, it is preferred to heat the compound of the formula (IV) in a solvent such as high boiling point hydrocarbons or high boiling point ethers, for example, tetralin diphenyl ether, diethylene glycol dimethyl ether, etc. at a temperature of about 100° to about 250° C., preferably 150° to 200° C. for a period of about 0.5 to about 6 hours. When the cyclization is effected using an acidic substance, the cyclization can be effected in the presence of the acid substance in an approximately equimolar amount to a large excess amount, preferably 10 to 20 molar excess amount, relative to the amount of the compound of the formula (IV) at a temperature of about 100° to about 150° C. for a period of about 0.5 to about 6 hours, whereby the desired pyrido[3,2,1-jk]carbazol derivatives of the formula (I) can be produced advantageously.

The compounds of the formula (I) wherein R represents an alkoxy group which may be substituted with a halogen atom or a 4-methyl-1-piperidinyl group, or a hydroxy group, i.e., the compounds of the formula (Ia) or (Ib), can be produced from each other by hydrolysis or esterification as shown by the Reaction Scheme—II below.

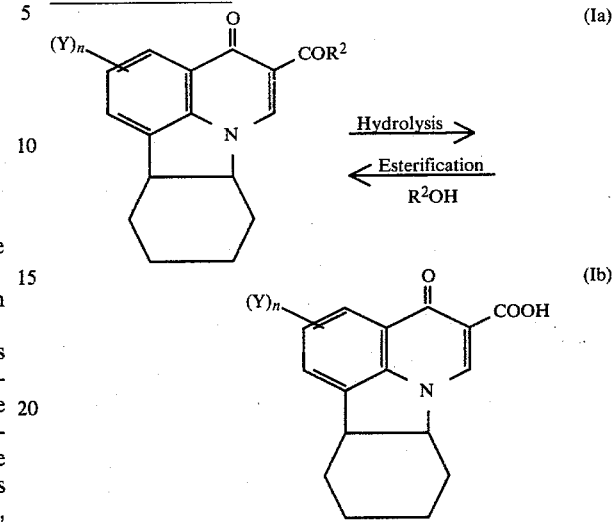

wherein Y and n are as defined above, and $R^2$ represents an alkoxy group which may be substituted with a halogen atom or a 4-methyl-1-piperidinyl group.

In the above Reaction Scheme—II, the hydrolysis of the compound of the formula (Ia) into the compound of the formula (Ib) can be achieved by a conventional hydrolysis procedure in the presence of a usual catalyst, for example, a basic compound such as sodium hydroxide, potassium hydroxide, barium hydroxide and the like, or an inorganic or organic acid such as sulfuric acid, hydrochloric acid, nitric acid, acetic acid, an aromatic sulfuric acid and the like. The hydrolysis can be carried out in a solvent such as water, methanol, ethanol, isopropanol, acetone, methyl ethyl ketone, dioxane, ethylene glycol, acetic acid and the like at a temperature of from room temperature to about 200° C., preferably 50° to 150° C. for a period of about 0.5 to about 6 hours.

The esterification of the compound of the formula (Ib) into the compound of the formula (Ia) can be achieved by a usual esterification procedure, for example, a method using a carboxylic acid, an acid halide or an acid anhydride.

The esterification using the carboxylic acid [Formula (Ib)] can be carried out in the presence of a catalyst generally used in the esterification, for example, an inorganic acid such as hydrogen chloride gas, concentrated sulfuric acid, phosphoric acid, polyphosphoric acid, boron trifluoride, perchloric acid and the like, an organic acid such as trifluoroacetic acid, trichloromethanesulfonic acid, naphthalenesulfonic acid, p-toluenesulfonic acid, benzenesulfonic acid, ethanesulfonic acid and the like, an acid anhydride such as trichloromethanesulfonic anhydride, trifluoromethanesulfonic anhydride and the like, or thionyl chloride and the like.

The esterification reaction can be carried out in the presence or absence of a solvent. Examples of solvents which can be used are aromatic hydrocarbons such as benzene, toluene, xylene and the like, halogenated hydrocarbons such as dichloromethane, dichloroethane, chloroform, carbon tetrachloride and the like, ethers such as diethyl ether, tetrahydrofuran, dioxane, ethylene glycol monomethyl ether and the like.

The amount of an alcohol having the formula $R^2OH$ wherein $R^2$ is as defined above, used in the esterification is not critical and can be over an approximately equimolar amount relative to the compound of the formula (Ib), but is preferably a molar excess amount in the absence of solvents and is about 1 to about 5 mols, preferably 1 to 2 mols, per mol of the compound of the formula (Ib). This esterification can be carried out at a temperature of about $-20°$ to about 200° C., preferably 0° to 150° C. for a period of about 0.5 to about 6 hours.

The esterification using an acid halide of the compound of the formula (Ib) can be achieved by reacting an acid halide, which is prepared from the compound of the formula (Ib) and a suitable halogenating agent, with an alcohol of the formula $R^2OH$ wherein $R^2$ is as defined above.

The halogenation reaction between the compound of the formula (Ib) and the halogenating agent can be conducted in the presence or absence of solvents. Suitable examples of halogenating agents are thionyl chloride, phosphorus oxychloride, phosphorus oxybromide, phosphorus pentachloride, phosphorus pentabromide and the like. Suitable examples of solvents which can be used in the halogenation reaction are aromatic hydrocarbons such as benzene, toluene, xylene and the like, halogenated hydrocarbons such as dichloromethane, dichloroethane, chloroform, carbon tetrachloride and the like, ethers such as diethyl ether, tetrahydrofuran, dioxane, ethylene glycol dimethyl ether and the like. The halogenating agent can be used in a large molar excess amount relative to the compound of the formula (Ib) in the absence of solvents, or in an amount of at least an equimolar amount, preferably 1 to 2 mols, per mol of the compound of the formula (Ib) in the presence of solvents. The halogenation reaction can be conducted at a temperature of from room temperature to about 100° C., preferably room temperature to 50° C., for about 1 to 3 hours.

The reaction between the acid halide of the compound of the formula (Ib) prepared above and an alcohol of the formula $R^2OH$ wherein $R^2$ is as defined above can be carried out with or without using solvents in the presence of a hydrogen haldie acceptor. Suitable examples of solvents are aromatic hydrocarbon such as benzene, toluene, xylene and the like, halogenated hydrocarbons such as dichloromethane, dichloroethane, chloroform, carbon tetrachloride and the like, ethers such as diethyl ether, tetrahydrofuran, dioxane, ethylene glycol dimethyl ether and the like, pyridine and the like. Suitable examples of hydrogen halide acceptors are inorganic basic compounds such as sodium carbonate, sodium bicarbonate, potassium carbonate and the like, and tertiary amines such as triethylamine, pyridine, quinoline, N,N-dimethylaniline and the like. Such hydrogen halide acceptors can be used in an amount of at least equimolar amount, preferably 1 to 2 mols, per mol of the acid halide of the compound of the formula (Ib). The reaction can be carried out at a temperature of about $-10°$ C. to about 50° C., preferably 0° C. to room temperature, for a period of about 30 minutes to about 6 hours.

The alcohol of the formula $R^2OH$ can be used in a large molar excess relative to the acid halide of the compound of the formula (Ib) when the reaction is carried out in the absence of solvent, or in an amount of at least equimolar amount, preferably 1 to 2 mols, per mol of the acid halide of the compound of the formula (Ib) when the reaction is carried out in a solvent.

The pyrido[3,2,1-jk]carbazol derivatives represented by the formula (I) wherein R represents a hydrazino group or a

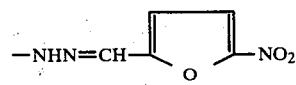

group, i.e., the compounds of the formula (Id) or (Ie), can also be prepared by the following Reaction Scheme-III.

Reaction Scheme - III

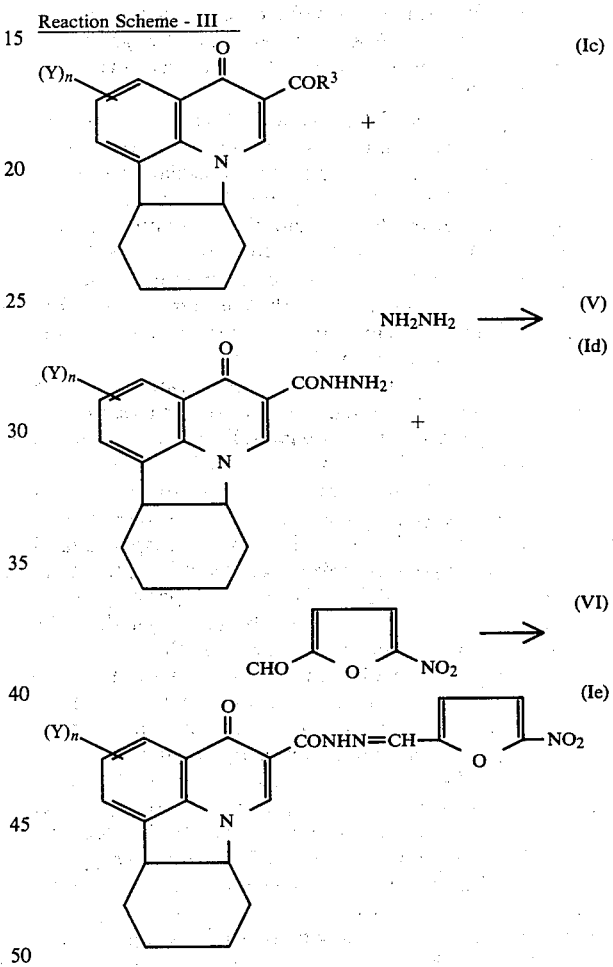

wherein Y and n are as defined above, and $R^3$ represents an alkoxy group.

The reaction of the compound of the formula (Ic) with hydrazine of the formula (V) can be carried out in a solvent. Examples of solvents are aromatic hydrocarbons such as benzene, toluene, xylene and the like, lower alcohols such as methanol, ethanol, propanol and the like, ethers such as diethyl ether, tetrahydrofuran, dioxane, ethylene glycol monomethyl ether and the like, dimethyl sulfoxide dimethylformamide and the like.

The reaction can be carried out under pressurized conditions, i.e., at a pressure of about 1 to about 10 atms., preferably 1 to 5 atms., at a temperature of about 50° to about 150° C., preferably 60° to 100° C. for a period of about 1 to about 5 hours, using at least an equimolar amount, preferably 1 to 2 mols, of hydrazine of the formula (V) per mol of the compound of the formula (Ic).

The subsequent reaction of the compound of the formula (Id) thus obtained and the compound of the formula (IV) can be carried out in a solvent. Examples of solvents which can be used are lower alcohols such as methanol, ethanol, propanol and the like, aromatic hydrocarbons such as benzene, toluene, xylene and the like, ethers such as diethyl ether, tetrahydrofuran, dioxane, ethylene glycol monomethyl ether and the like, dimethyl sulfoxide, dimethylformamide and the like. The reaction can be carried out at a temperature of from about room temperature to about 120° C., preferably 50° to 100° C. for a period of about 10 minutes to about 1 hour using at least an equimolar amount, preferably 1 to 2 mols, of the compound of the formula (IV) per mol of the compound of the formula (Id).

The compound of the formula (I) wherein R represents an alkoxy group substituted with a 4-methyl-1-piperidinyl group, i.e., the compounds of the formula (Ig) below can also be prepared by the Reaction Scheme-IV.

Reaction Scheme - IV

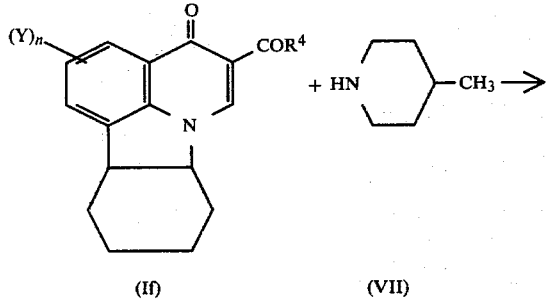

(If)    (VII)

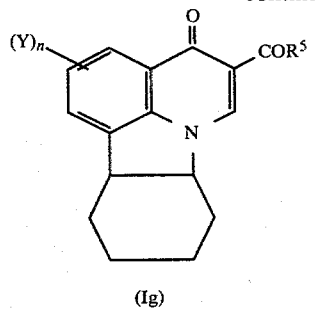

(Ig)

wherein Y and n are as defined above, $R^4$ represents an alkoxy group substituted with a halogen atom and $R^5$ represents an alkoxy group substituted with a 4-methyl-1-piperidinyl group.

The reaction of the compound of the formula (If) with 4-methylpiperidine of the formula (VII) can be carried out in a solvent in the presence of a basic compound. Examples of solvents which can be used are aromatic hydrocarbons such as benzene, toluene, xylene and the like, ethers such as diethyl ether, tetrahydrofuran, dioxane, ethylene glycol monomethyl ether and the like, dimethyl sulfoxide, dimethylformamide and the like. Examples of basic compounds which can be used are sodium amide, potassium amide, sodium hydroxide, potassium hydroxide, sodium carbonate, sodium bicarbonate, potassium carbonate and the like.

The reaction of the compound of the formula (If) with 4-methylpiperazine of the formula (VII) can be carried out at a temperature of about 50° to about 200° C., preferably 80° to 150° C., for a period of about 2 to about 10 hours. In this reaction, 4-methylpiperidine of the formula (VII) and the basic compound can be used in an amount of at least an equimolar amount, preferably 1 to 2 mols, per mol of the compound of the formula (If).

The compounds of the formula (I) wherein Y represents an amino group, an alkanoylamino group, a hydrogen atom or a halogen atom can also be prepared from the compound of the formula (I) wherein Y represents a nitro group, i.e., the compounds of the formula (Ih) by the following Reaction Scheme-V.

Reaction Scheme - V

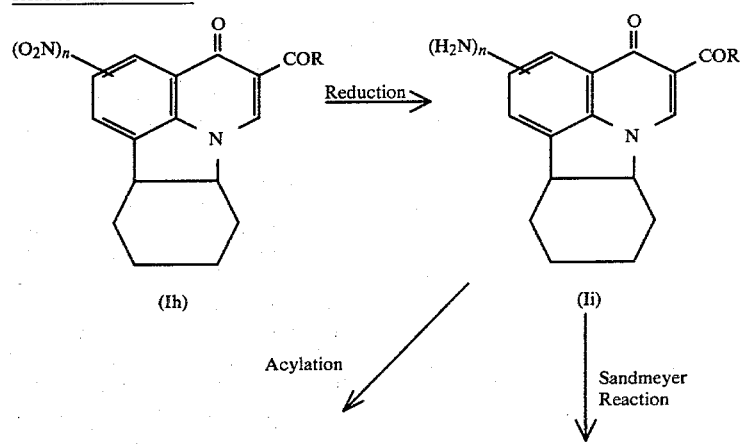

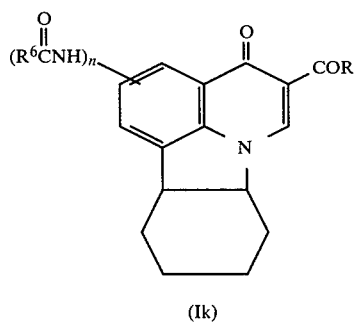 (Ik)

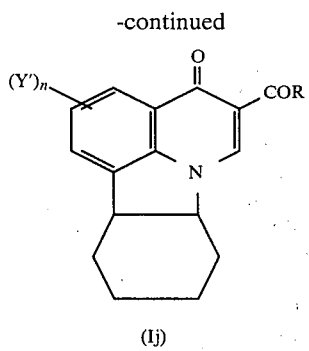 (Ij)

wherein R and n are as defined above, $R^6$ represents an alkyl group and Y' represents a hydrogen atom or a halogen atom.

In the alternative procedures shown in the Reaction Scheme-V above, the reduction reaction of the compound of the formula (Ih) can be conducted using (1) a conventional reducing agent such as a combination of iron and hydrochloric acid; zinc and acetic acid; tin or stannous chloride and hydrochloric acid; or the like in at least an equimolar amount, preferably 3 to 5 mols, per mol of the compound of the formula (Ih) or (2) a conventional hydrogenation catalyst such as palladium black, palladium carbon, Raney nickel, platinum dioxide and the like. The reduction proceeds advantageously in water, an alcohol such as methanol, ethanol, isopropanol and the like, acetic acid, etc., at a temperature of about 0° to about 150° C., preferably 50° to 100° C. in the presence of the reducing agent described above or at a temperature of about 0° to about 100° C., preferably at room temperature in a hydrogen atmosphere under atmospheric pressure or pressurized conditions in the presence of the hydrogenation catalyst described above.

The Sandmeyer reaction of the compound of the formula (Ii) in Reaction Scheme-V can be effected by diazotizing the compound of the formula (Ii) with an aqueous solution of sodium nitrite and hydrochloric acid or sulfuric acid at a temperature of about −30° C. to room temperature and then reacting the resulting diazo compound with ethanol, cuprous chloride, cuprous bromide, potassium iodide, bromine or tetrafluoroboron hydride at a temperature of about 0° to about 100° C.

The acylation reaction of the compounds of the formula (Ii) in Reaction Scheme-V can generally be conducted with or without using an inert solvent, for example, pyridine, chloroform, water and the like using an acid anhydride or an acid halide of an aliphatic acid as an acylating agent in the presence of a basic compound such as a tertiary amine, for example, pyridine, triethylamine, trimethylamine and the like, an alkali metal bicarbonate or hydroxide, for example, potassium bicarbonate, sodium bicarbonate, sodium hydroxide, potassium hydroxide and the like, at a temperature of about 0° to about 100° C., preferably 0 to room temperature. The acylating agent is advantageously used in an amount at least an equimolar amount, preferably 1 to 5 mols, per mol of the compound of the formula (Ii).

Further, the compounds of the present invention represented by the formula (I) wherein Y represents an alkyl group can also be prepared by Wittig reaction from the compounds of the formula (I) wherein Y represents a halogen atom obtained as described above. Also, the compounds of the formula (I) wherein Y represents a halogen atom or a nitro group can be prepared from the compound of the formula (I) wherein Y represents a hydrogen atom by usual halogenation or nitration, respectively, using a conventional halogenating agent or nitrating agent.

The pyrido[3,2,1-jk]carbazol derivatives represented by the formula (I) prepared as described above can form pharmaceutically acceptable salts with acids when the compound of the formula (I) has a basic group, and the present invention includes within its scope such pharmaceutically acceptable salts. The pharmaceutically acceptable acids which can be used for the salt formation can be various organic or inorganic acids, for example, hydrochloric acid, sulfuric acid, nitric acid, hydrobromic acid, phosphoric acid, acetic acid, oxalic acid, malonic acid, succinic acid, maleic acid, fumaric acid, malic acid, mandelic acid, ethanesulfonic acid, p-toluenesulfonic acid and the like.

The compounds of the formula (I) wherein R represents a hydroxy group, i.e., a carboxylic acid, can be converted into a corresponding carboxylate by reacting the carboxylic acid with a pharmaceutically acceptable basic compound. Examples of basic compounds are inorganic basic compounds such as sodium hydroxide, potassium hydroxide, calcium hydroxide, aluminum hydroxide, sodium bicarbonate and the like and organic basic compounds such as morpholine, piperazine, pyridine, piperidine, ethylamine, dimethylamine, triethylamine, aniline and the like.

The pyrido[3,2,1-jk]carbazol derivatives and the salts thereof represented by the formula (I) obtained as described above can be isolated from the respective reaction mixtures upon completion and purified by conventional procedures, for example, solvent extraction, dilution method, precipitation method, recrystallization method, column chromatography, preparative thin layer chromatography and the like.

As is apparent to those skilled in the art, the pyrido[3,2,1-jk]carbazole derivatives of the formula (I) can exist in optically active forms and the present invention includes such optical isomers within the scope of the invention.

In using the compounds of the present invention of the formula (I) and the salts thereof as therapeutic agents, these compounds can be formulated into pharmaceutical compositions together with ordinary pharmaceutically acceptable carriers. Suitable carriers which can be used are, for example, diluents or excipients such as fillers, extenders, binders, wetting agents, disintegrants, surface active agents and lubricants which are usually employed to prepare such drugs depending on the type of dosage forms.

Various dosage forms of the therapeutic agents as a antimicrobial agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, painalleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as an antimicrobial agent is not particularly limited, and can vary over a wide range. A suitable therapeutically effective amount of the compound of the general formula (I) and the pharmaceutically acceptable salts thereof of this invention is usually about 1 to about 70% by weight, preferably 5 to 50% by weight, based on the entire composition.

There is no particular restriction on the manner of using the therapeutic agent as a nephritis treating agent, and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be singly administered intramuscularly, intracutaneously, subcutaneously, or intraperitoneally. The suppository is administered intrarectally.

The dosage of the antimicrobial agent is suitably selected according to the purpose of use, the symptoms, etc. Usually, a preferred dosage of the compound of this invention is about 10 mg of 5 g/body per day in 3 to 4 multiple doses.

The present invention is further illustrated by the following Reference Examples (preparation of starting materials) and Examples, but they are not to be construed as limiting the scope of this invention. The antimicrobial activity of typical compounds of the present invention are also shown in Examples. Unless otherwise indicated, all parts, percents and ratios are by weight.

REFERENCE EXAMPLE 1

12.6 g of p-fluoroaniline was dissolved in 100 ml of ethanol and a catalytic amount of p-toluenesulfonic acid was added thereto. 9.8 g of cyclohexanone was then added dropwise to the mixture at room temperature. After completion of the addition, the mixture was stirred at room temperature for one hour and concentrated under reduced pressure. Dilute sulfuric acid prepared from 190 ml of water and 20 ml of concentrated sulfuric acid was added to the residue and the mixture was heated at 110° C. for 15 minutes on an oil bath to precipitate light orange crystals. The crystals thus formed were filtered, washed 3 times with water and dried to obtain 17.4 g of 6-fluoro-1,2,3,4-tetrahydrocarbazol which was identified by NMR spectrum.

REFERENCE EXAMPLE 2

10 g of 6-fluoro-1,2,3,4-tetrahydrocarbazol was dissolved in 75 ml of glacial acetic acid and 15 g of tin metal was added to the solution. The mixture was heated on an oil bath while refluxing and then 50 ml of concentrated hydrochloric acid was added dropwise thereto. The color of the reaction system changed from orange color to colorless with vigorous generation of hydrogen. After reaction for 3.5 hours, any excess of tin metal was removed by filtration, and the filtrate was concentrated. 50 ml of water was added to the residue, and the mixture was rendered alkaline with 4 N sodium hydroxide and extracted with diethyl ether. The ether layer was dried over anhydrous sodium sulfate, filtered and concentrated to obtain 10 g of 6-fluoro-1,2,3,4,10,11-hexahydrocarbazol as white crystals having a melting point of 80°–83° C. The production of the above compound was confirmed by NMR spectrum.

EXAMPLE 1

9 g of ethyl ethoxymethylenemalonate was added to 8 g of 6-fluoro-1,2,3,4,10,11-hexahydrocarbazol and the mixture was heated at 110° C. on an oil bath during which time distillation of ethanol was observed. After heating the mixture at the same temperature as above for 30 minutes, 100 g of polyphosphoric acid was added thereto followed by heating at 140° C. for 30 minutes. After completion of the reaction, the reaction mixture was poured into 500 ml of water to obtain light brown crystals which were then recrystallized from a mixture of benzene-hexane (1:1) to obtain 14 g of ethyl 2-fluoro-7a,8,9,10,11,11a-hexahydro-4-oxo-4H-pyrido-[3,2,1-jk]carbazol-5-carboxylate as white plates having a melting point of 97°-98° C.

EXAMPLE 2

21.6 g of ethyl ethoxymethylenemalonate was added to 17.5 g of 1,2,3,4,10,11-hexahydrocarbazol and the mixture was heated at 110° C. on an oil bath for 30 minutes while stirring, during which time distillation of ethanol was observed. After heating, 240 g of polyphosphoric acid prepared from 120 g of phosphoric acid and 120 g of phosphorus pentoxide was added to the mixture and the mixture was allowed to react on an oil bath at 140° C. for 45 minutes. After completion of the reaction, the mixture was allowed to cool to room temperature and poured into 400 ml of water, followed by rendering the mixture neutral with 40% aqueous sodium hydroxide to precipitate light purple crystals. The crystals thus obtained were recrystallized from benzene-hexane (1:1) to obtain 32 g of ethyl 7a,8,9,10,11,11a-hexahydro-4-oxo-4H-pyrido[3,2,1-kj]carbazol-5-carboxylate having a melting point of 71°-73° C.

EXAMPLE 3

8.36 g (0.0387 mol) of ethyl ethoxymethylenemalonate was added to 7.32 g (0.0387 mol) of 6-methyl-1,2,3,4,10,11-hexahydrocarbazol and the mixture was heated on an oil bath at 110° C., during which time distillation of ethanol was observed. After heating the mixture at the same temperature as above, 100 g of polyphosphoric acid was added thereto followed by heating at 140° C. for 40 minutes. After completion of the reaction, the reaction mixture was poured into 200 ml of water and the resulting mixture was rendered neutral with 20% aqueous sodium hydroxide while cooling to precipitate light brown crystals which were recrystallized from benzene-hexane (1:1) to obtain 12 g of ethyl 2-methyl-7a,8,9,10,11,11a-hexahydro-4-oxo-4H-pyrido[3,2,1-jk]carbazol-5-carboxylate as colorless plates having a melting point of 107°-109° C.

EXAMPLES 4-17

In the same manner as described in the above Examples, the following compounds having various substituents shown in Table 1 below were prepared. The melting point and the crystal form of the resulting products are also shown in Table 1.

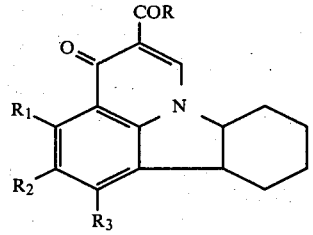

TABLE 1

| Example Nos. | R | $R_1$ | $R_2$ | $R_3$ | Melting Point (°C.) | Crystal Form (Recrystallization Solvent) |
|---|---|---|---|---|---|---|
| 4 | $OC_2H_5$ | H | Cl | H | 93-95 | Light Yellow Amorphous (Benzene - Hexane) |
| 5 | OH | H | $CH_3O$ | H | 198-200 | Light Yellow Amorphous (Chloroform - Hexane) |
| 6 | OH | H | Cl | H | 219-221 | Light Yellow Amorphous (Chloroform - Hexane) |
| 7 | OH | $CH_3$ | H | $CH_3$ | 216-217 | Light Brown Needles (Ethanol) |
| 8 | OH | F | H | H | 215-217 | Light Yellow Plates (Ethanol) |
| 9 | OH | H | H | H | 238-241 | Light Yellow Amorphous (Chloroform - Hexane) |
| 10 | OH | H | F | H | 281-282 | White Needles (Ethanol) |
| 11 | OH | $NO_2$ | H | H | 251-253 | Yellow Amorphous (DMF - $H_2O$) |
| 12 | OH | $NH_2$ | H | H | 253-256 (Decomposition) | Light Yellow Amorphous (DMF - $H_2O$) |
| 13 | OH | $NHCOCH_3$ | H | H | 187-190 | Light Yellow Amorphous (DMF - $H_2O$) |
| 14 | $NHNH_2$ | H | F | H | 228-230 | Light Yellow Needles (Ethanol) |
| 15 | $OCH_2CH_2Br$ | H | F | H | 126-127 | White Plates (Toluene) |
| 16 | 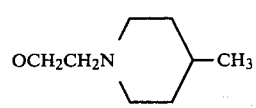 | H | F | H | 187-192 (Hydrochloride) | Colorless Amorphous |

TABLE 1-continued

| Example Nos. | R | R1 | R2 | R3 | Melting Point (°C.) | Crystal Form (Recrystallization Solvent) |
|---|---|---|---|---|---|---|
| 18 | 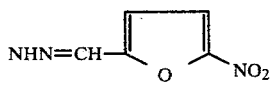 | | H | F | H | 293-294 (Decomposition) | Colorless Amorphous |

EXAMPLE 18

140 ml of a 10% aqueous sodium hydroxide solution was added to 10 g of ethyl 2-fluoro-7a,8,9,10,11,11a-hexahydro-4-oxo-4H-pyrido[3,2,1-jk]carbazol-5-carboxylate, followed by heat-refluxing for 40 minutes. The crystals of the above starting material were dissolved to give a uniform solution. The solution was treated with activated carbon while hot, and filtered. The filtrate was cooled, and adjusted to pH 2 with concentrated hydrochloric acid to obtain 8 g of white crystals. The resulting crystals were recrystallized from ethanol to give 2-fluoro-7a,8,9,10,11,11a-hexahydro-4-oxo-4H-pyrido[3,2,1-jk]carbazol-5-carboxylic acid as white needles having a melting point of 281°-282° C.

EXAMPLE 19

250 ml of a 10% aqueous sodium hydroxide solution was added to 28 g of ethyl 7a,8,9,10,11,11a-hexahydro-4-oxo-4H-pyrido[3,2,1-jk]carbazol-5-carboxylate, followed by heat-refluxing for 2 hours. The reaction system changed from a suspension state to a uniform solution as the reaction proceeded. 200 ml of water was added to the reaction mixture which was then filtered, and the filtrate was rendered acidic with concentrated hydrochloric acid to precipitate light yellow crystals. The crystals were separated by filtration, washed successively with water and a small amount of ethanol, dried and recrystallized from chloroform-hexane (1:1 by volume) to obtain 16 g of 7a,8,9,10,11,11a-hexahydro-4-oxo-4H-pyrido[3,2,1-jk]carbazol-5-carboxylic acid as light yellow amorphous crystals having a melting point of 238°-241° C.

EXAMPLE 20

70 ml of a 10% aqueous sodium hydroxide solution was added to 4 g of ethyl 2-methyl-7a,8,9,10,11,11a-hexahydro-4-oxo-4H-pyrido[3,2,1-jk]carbazol-5-carboxylate. The mixture was heat-refluxed for 1.5 hours, allowed to cool to room temperature and filtered. The filtrate was cooled and adjusted to a pH of 2 with concentrated hydrochloric acid to obtain 3.2 g of light yellow crystals. Recrystallization from ethanol gave 2-methyl-7a,8,9,10,11,11a-hexahydro-4-oxo-4H-pyrido[3,2,1-jk]carbazol-5-carboxylic acid as needle crystals having a melting point of 188°-190° C.

EXAMPLES 21 TO 24

In the same manner as described in Examples 18 to 20, the following compounds having the substituents shown in Table 2 below were prepared. The melting point and the crystal form of the resulting products are also shown in Table 2.

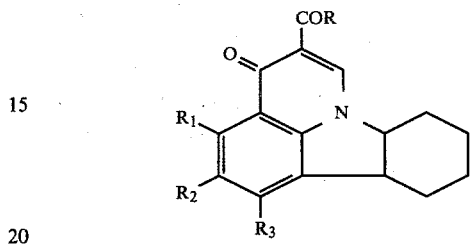

TABLE 2

| Ex. Nos. | R | R1 | R2 | R3 | Melting Point (°C.) | Crystal Form (Recrystallization Solvent) |
|---|---|---|---|---|---|---|
| 21 | OH | H | OCH3 | H | 198-200 | Light Yellow Amorphous (Chloroform - Hexane |
| 22 | OH | H | Cl | H | 219-221 | Light Yellow Amorphous (Chloroform - Hexane |
| 23 | OH | CH3 | H | CH3 | 216-217 | Light Brown Needles (Ethanol) |
| 24 | OH | F | H | H | 215-217 | Light Yellow Plates (Ethanol) |

EXAMPLE 25

6 g of 3-nitro-7a,8,9,10,11,11a-hexahydro-4-oxo-4H-pyrido[3,2,1-jk]carbazol-5-carboxylic acid was dissolved in 100 ml of a 2% aqueous potassium hydroxide solution and the solution was catalytically reduced by the Parr method (3 kg/cm$^2$) in the presence of 5 g of Raney nickel. After completion of the reduction, the mixture was filtered and the filter cake on the filter paper was washed with water and the combined filtrate and the washing was rendered neutral with glacial acetic acid to precipitate brown crystals. The resulting crystals were filtered, washed with water, dried and recrystallized from DMF-H$_2$O to obtain 3.7 g of 3-amino-7a,8,9,10,11,11a-hexahydro-4-oxo-4H-pyrido[3,2,1-jk]carbazol-5-carboxylic acid having a melting point of 253°-356° C. (with decomposition).

EXAMPLE 26

2.84 g of 3-amino-7a,8,9,10,11,11a-hexahydro-4-oxo-4H-pyrido[3,2,1-jk]carbazol-5-carboxylic acid was dissolved in 50 ml of a 2% aqueous potassium hydroxide, and acetic anhydride was added dropwise thereto while ice cooling whereby orange-colored crystals were precipitated. The resulting crystals were separated by filtration, washed with water and recrystallized from dimethylformamide-water to obtain 3 g of 3-acetylamino-7a,8,9,10,11,11a-hexahydro-4-oxo-4H-pyrido[3,2,1-jk]carbazol-5-carboxylic acid having a melting point of 187°-190° C.

EXAMPLE 27

6 g of 7a,8,9,10,11,11a-hexahydro-4-oxo-4H-pyrido[3,2,1-jk]carbazol-5-carboxylic acid was dissolved in 35 ml of concentrated sulfuric acid and stirred while cooling with ice, followed by dropwise addition of a mixture of 4.3 ml of concentrated nitric acid having a specific gravity and 15 ml of the concentrated sulfuric acid. After completion of the addition, the resulting mixture was stirred for one hour at room temperature and poured into 200 g of ice to precipitate yellow crystals. Recrystallization from dimethylformamide-water gave 7 g of 3-nitro-7a,8,9,10,11,11a-hexahydro-4-oxo-4H-pyrido[3,2,1-jk]carbazol-5-carboxylic acid having a melting point of 251°-253° C.

EXAMPLE 28

5.64 g of 2-fluoro-7a,8,9,10,11,11a-hexahydro-4-oxo-4H-pyrido[3,2,1-jk]carbazol-5-carboxylic acid was suspended in 60 ml of chloroform and 4.5 g of phosphorus pentachloride was added to the suspension at room temperature. After allowing the mixture to react at room temperature for 30 minutes, the solvent was removed under reduced pressure to obtain a carboxylic acid chloride as a light brown oily substance. 60 ml of chloroform was added to the resulting carboxylic acid chloride, and 3 g of ethylenebromohydrin was added dropwise to the solution. After stirring the mixture for one hour at room temperature, 50 ml of a saturated aqueous solution of potassium carbonate was added to the mixture and the chloroform layer was separated. The chloroform layer was washed with water, dried over anhydrous sodium sulfate and the chloroform was removed to obtain 6.7 g of β-bromoethyl 2-fluoro-7a,8,9,10,11,11a-hexahydro-4-oxo-4H-pyrido[3,2,1-jk]carbazol-5-carboxylate. Recrystallization from toluene gave a product as white plate crystals having a melting point of 126°-217° C.

EXAMPLE 29

3 g of β-bromoethyl 2-fluoro-7a,8,9,10,11,11a-hexahydro-4-oxo-4H-pyrido[3,2,1-jk]carbazol-5-carboxylate was added to a suspension of 1 g of 4-methylpiperidine and 0.4 g of sodium amide in 30 ml of toluene, and the mixture was heated for 5 hours while refluxing. After the reaction had been completed as confirmed by the thin layer chromatography, a saturated aqueous solution of sodium carbonate was added to the reaction mixture and the toluene layer was separated. The toluene layer was dried over anhydrous sodium sulfate, concentrated to a volume of 15 ml and hydrogen chloride gas was introduced into the solution, followed by removal of toluene under reduced pressure. 10 ml of diethyl ether was added to the resulting residue and the mixture was triturated to obtain 2.3 g of β-(4-methyl-1-piperidinyl)ethyl 2-fluoro-7a,8,9,10,11,11a-hexahydro-4-oxo-4H-pyrido[3,2,1-jk]carbazol-5-carboxylate hydrochloride as colorless amorphous crystals having a melting point of 187°-192° C.

EXAMPLE 30

2 g of ethyl 2-fluoro-7a,8,9,10,11,11a-hexahydro-4-oxo-4H-pyrido[3,2,1-jk]carbazol-5-carboxylate was dissolved in 80 ml of methanol, and 5 ml of hydrazine hydrate was added thereto. The mixture was then heated while refluxing. The precipitated yellow needle crystals were separated by filtration, and recrystallized from ethanol to obtain 1.7 g of 2-fluoro-7a,8,9,10,11,11a-hexahydro-4-oxo-4H-pyrido[3,2,1-jk]carbazol-5-carbohydrazide monohydrate.

EXAMPLE 31

20 ml of ethanol was added to 1.6 g of the hydrazide prepared as described in Example 30, and 0.8 g of 5-nitro-2-furaldehyde was added to the solution while heat-refluxing. The mixture was then heat-refluxed for 10 minutes, and the yellow crystals precipitated was filtered after cooling, washed with ethanol and dried to obtain 1.8 g of 2-fluoro-7a,8,9,10,11,11a-hexahydro-4-oxo-4H-pyrido[3,2,1-jk]carbazol-5-carboxylic acid 5-nitrofurfurylidene hydrazide as colorless amorphous crystals having a melting point of 293°-294° C. (with decomposition).

Antimicrobial Activity

1. Test Method

The antimicrobial activity of the following test compounds on various test organisms listed below was determined by the serial dilution method on agar plate and the minimum inhibitory concentration (mcg/ml) obtained are shown in Table 4 below.

2. Test Organisms

A. *Bacillus subtilis* ATCC 6633
B. *Bacillus anthracis*
C. *Bacillus cereus* ATCC 11778
D. *Staphyrococcus aureus* FDA 209p
E. *Staphyrococcus aureus* Newmann
F. *Streptococcus faecalis* IFO 12580
G. *Streptomyces viridans*
H. *Sarcina lutea* ATCC 9341
I. *Micrococcus flavus* ATCC 10240a
J. *Serratia marcescens* ATCC 14756
K. *Salmonella typhimurium* kh
L. *Enterbactor cloacae* 2
M. *Enterbactor aerogenes* IFO 12979
N. *Klebsiella pneumoniae* ST-101
O. *Esherichia coli* NIHJ
P. *Esherichia coli* NIHJ JC-2
Q. *Proteus mirabilis* 1287
R. *Pseudomonas aeruginosa* ATCC 10145
S. *Candida albicans* KYU 3. Test Compounds The compounds tested are shown in Table 3 below where Compound Nos. 1 to 12 are the compounds of this invention represented by the formula (I), Compound No. 13 is nalidixic acid (1-ethyl-1,4-dihydro-7-methyl-4-one-1,8-naphthyridine-3-carboxylic acid) as a control.

TABLE 3

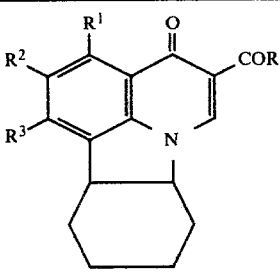

| Test Compound No. | $R^1$ | $R^2$ | $R^3$ | R |
|---|---|---|---|---|
| 1 | H | F | H | OH |
| 2 | H | H | H | OH |
| 3 | H | F | H | $OC_2H_5$ |
| 4 | H | $OCH_3$ | H | OH |
| 5 | $CH_3$ | H | $CH_3$ | OH |
| 6 | $NO_2$ | H | H | OH |
| 7 | $NH_2$ | H | H | OH |
| 8 | $CH_3CONH$ | H | H | OH |
| 9 | H | F | H | $OCH_2CH_2Br$ |
| 10 | H | F | H | $NHNH_2$ |
| 11 | H | F | H | $NHN=CH-\text{(furan)}-NO_2$ |
| 12 | H | F | H | $OCH_2CH_2N\text{(piperidine)}-CH_3$ |
| 13 | Nalidixic Acid | | | |

TABLE 4

Minimum Inhibitory Concentration (MIC) (mcg/ml)

| Test Organism | 1 | 2 | 3 | 4 | 5 | 6 | 7 | 8 | 9 | 10 | 11 | 12 | 13 |
|---|---|---|---|---|---|---|---|---|---|---|---|---|---|
| A | 1.6 | 12.5 | 6.3 | 3.2 | 6.3 | 3.2 | 6.3 | 3.2 | 12.5 | 25 | 3.2 | 3.2 | 6.3 |
| B | 3.2 | 25 | 50 | 6.3 | 6.3 | 12.5 | 12.5 | 6.3 | 50 | 100 | 6.3 | 6.3 | 12.5 |
| C | 25 | 100 | 100 | 12.5 | 25 | 12.5 | 50 | 50 | 100 | 100 | 12.5 | 6.3 | 50 |
| D | 6.3 | 25 | 25 | 12.5 | 6.3 | 12.5 | 50 | 12.5 | 50 | 50 | 12.5 | 6.3 | 50 |
| E | 6.3 | 25 | 25 | 12.5 | 6.3 | 12.5 | 50 | 12.5 | 50 | 50 | 12.5 | 6.3 | 50 |
| F | 100 | >100 | >100 | 100 | >100 | >100 | >100 | 100 | >100 | >100 | >100 | 50 | >100 |
| G | 100 | >100 | >100 | 100 | >100 | >100 | >100 | 100 | >100 | >100 | >100 | 100 | >100 |
| H | 50 | 100 | 100 | 100 | 100 | 50 | >100 | 50 | 100 | >100 | 100 | 50 | >100 |
| I | 50 | 100 | 100 | 100 | 100 | 50 | >100 | 50 | 100 | >100 | 100 | 50 | >100 |
| J | 3.2 | 12.5 | 25 | 12.5 | 6.3 | 6.3 | 12.5 | 3.2 | 12.5 | 25 | 12.5 | 12.5 | 3.2 |
| K | 6.3 | 25 | 25 | 12.5 | 12.5 | 12.5 | 12.5 | 6.3 | 25 | 25 | 12.5 | 12.5 | 6.3 |
| L | 3.2 | 12.5 | 12.5 | 6.3 | 6.3 | 6.3 | 12.5 | 6.3 | 12.5 | 12.5 | 6.3 | 6.3 | 12.5 |
| M | 3.2 | 12.5 | 25 | 6.3 | 12.5 | 6.3 | 12.5 | 6.3 | 25 | 12.5 | 6.3 | 6.3 | 6.3 |
| N | 3.2 | 12.5 | 12.5 | 6.3 | 12.5 | 6.3 | 12.5 | 6.3 | 12.5 | 12.5 | 6.3 | 6.3 | 12.5 |
| O | 6.3 | 25 | 25 | 12.5 | 12.5 | 6.3 | 25 | 12.5 | 25 | 25 | 12.5 | 6.3 | 12.5 |
| P | 6.3 | 25 | 12.5 | 12.5 | 12.5 | 12.5 | 50 | 12.5 | 25 | 25 | 12.5 | 6.3 | 6.3 |
| Q | 12.5 | 50 | 25 | 25 | 12.5 | 12.5 | 50 | 25 | 50 | 50 | 12.5 | 12.5 | 25 |
| R | >100 | >100 | >100 | >100 | >100 | >100 | >100 | >100 | >100 | >100 | >100 | >100 | >100 |
| S | >500 | >500 | >500 | >500 | >500 | >500 | >500 | >500 | >500 | >500 | >500 | >500 | >500 |

Acute Toxicity

Further, the acute toxicity of the compounds of the present invention having the formula (I) was determined by intravenous administration (i.v.) and oral administration (p.o.) in 5 to 6 groups of rats (dd strain; body weight, 18 to 22 g; 10 rats in each group) which had been fasted for 12 hours prior to the test. Typical compounds of the present invention of the formula (I), i.e., the compounds of Sample Nos. 1 to 12 shown in Table 3 above, was found to have the $LD_{50}$ values (50% lethal dose) as shown in Table 5 below.

TABLE 5

| Test Compounds | $LD_{50}$(mg/kg) i.v. | p.o. |
|---|---|---|
| 1 | 130 | 5000 |
| 2 | 120 | 5000 |
| 3 | 80 | 3000 |
| 4 | 130 | 4000 |
| 5 | 120 | 3000 |
| 6 | 110 | 4000 |
| 7 | 115 | 4500 |
| 8 | 110 | 3500 |
| 9 | 105 | 3000 |
| 10 | 100 | 3500 |
| 11 | 180 | 3000 |

TABLE 5-continued

| Test Compounds | LD$_{50}$(mg/kg) | |
|---|---|---|
| | i.v. | p.o. |
| 12 | 130 | 2000 |

PREPARATION EXAMPLE 1

| | |
|---|---|
| Sodium salt of 2-Fluoro-7a, 8, 9, 10, 11, 11α-hexahydro-4-oxo-4H-pyrido[3,2,1-jk]carbazol-5-carboxylic acid | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

Preparation Example 2

| | |
|---|---|
| 2-Fluoro-7a, 8, 9, 10, 11, 11α-hexahydro-4-oxo-4H-pyrido-[3,2,1-jk]carbazol-5-carboxylic acid | 100 g |
| Avicel (Tradename of Asahi Kasei Kogyo Kabushiki Kaisha) | 40 g |
| Corn Starch | 30 g |
| Magnesium Stearate | 2 g |
| TC-5 (Tradename for hydroxypropyl-methyl cellulose, produced by Shinetsu Chemical Industry Co., Ltd.) | 10 g |
| Polyethylene Glycol-6000 (molecular weight, 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

Preparation Example 3

| | |
|---|---|
| Ethyl 2-fluoro-7a,8,9,10,11,11a-hexahydro-4-oxo-4H-pyrido[3,2,1-jk]carbazol-5-carboxylate | 2 g |
| Purified Hydrous Lanolin | 5 g |
| Japan wax | 5 g |
| White Petrolatum | 88 g |
| Total | 100 g |

Japan wax was heat-molten and the active compound, purified hydrous lanolin and white petroleum were added thereto followed by heat-melting. The mixture was stirred until it began to solidify to prepare an ointment.

What is claimed is:

1. A pyrido[3,2,1-jk]carbazol having the formula (I)

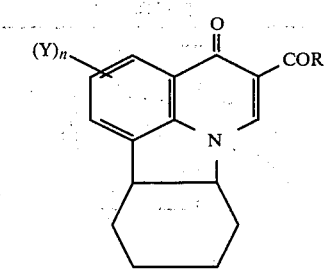

wherein R represents a hydroxy group, an alkoxy group having 1 to 4 carbon atoms, an alkoxy group having 1 to 4 carbon atoms and substituted with a halogen atom, an alkoxy group having 1 to 4 carbon atoms and substituted with a 4-methyl-1 piperidinyl group, a hydrazino group or a

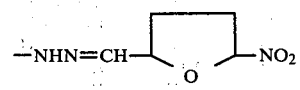

wherein Y represents a hydroxy group, an alkoxy group having 1 to 4 carbon atoms, a halogen atom, a nitro group, an amino group, an alkanoylamino group having 1 to 4 carbon atoms or non-sterically hindering alkyl group having 1 to 4 carbon atoms, and n is 0, 1 or 2; and the pharmaceutically acceptable salts thereof.

2. The pyrido[3,2,1-jk]carbazol and the pharmaceutically acceptable salts thereof according to claim 1, wherein Y represents a halogen atom.

3. The pyrido[3,2,1-jk]carbazol and the pharmaceutically acceptable salts thereof according to claim 1, wherein Y represents an alkoxy group, a nitro group, an amino group, an alkanoylamino group or an alkyl group.

4. The pyrido[3,2,1-jk]carbazol and the pharmaceutically acceptable salts thereof according to claim 2, wherein R represents a hydroxy group.

5. The pyrido[3,2,1-jk]carbazol and the pharmaceutically acceptable salts thereof according to claim 2, wherein R represents an alkoxy group which may be substituted with a halogen atom or a 4-methyl-1-piperidinyl group; a hydrazino group; or a

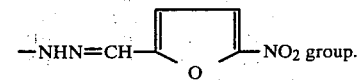

group.

6. The pyrido[3,2,1-jk]carbazol and the pharmaceutically acceptable salts thereof according to claim 3, wherein R represents a hydroxy group.

7. The pyrido[3,2,1-jk]carbazol and the pharmaceutically acceptable salts thereof according to claim 4, wherein n is 1.

8. 2-Fluoro-7a,8,9,10,11,11a-hexahydro-4-oxo-4H-pyrido[3,2,1-jk]carbazol-5-carboxylic acid, according to claim 1.

9. 1-Chloro-7a,8,9,10,11,11a-hexahydro-4-oxo-4H-pyrido[3,2,1-jk]carbazol-5-carboxylic acid, according to claim 1.

10. 2-Methoxy-7a,8,9,10,11,11a-hexahydro-4-oxo-4H-pyrido[3,2,1-jk]carbazol-5-carboxylic acid, according to claim 1.

11. 7a,8,9,10,11,11a-Hexahydro-4-oxo-4H-pyrido[3,2,1-jk]-carbazol-5-carboxylic acid, according to claim 1.

12. 1,3-Dimethyl-7a,8,9,10,11,11a-hexahydro-4-oxo-4H-pyrido[3,2,1-jk]carbazol-5-carboxylic acid, according to claim 1.

13. Ethyl 2-fluoro-7a,8,9,10,11,11a-hexahydro-4-oxo-4H-pyrido[3,2,1-jk]carbazol-5-carboxylate, according to claim 1.

14. 3-Acetylamino-7a,8,9,10,11,11a-hexahydro-4-oxo-4H-pyrido[3,2,1-jk]carbazol-5-carboxylic acid, according to claim 1.

* * * * *